United States Patent [19]

Quedens et al.

[11] Patent Number: 4,625,731

[45] Date of Patent: Dec. 2, 1986

[54] ULTRASONIC IMAGE DISPLAY MOUNTING

[75] Inventors: Phillip J. Quedens, Berlin; Peter J. Dutko, Jr., Durham; Raymond F. Larson, Middlefield; Ralph A. Donarumo, Wallingford, all of Conn.

[73] Assignee: Picker International, Inc., Highland Heights, Ohio

[21] Appl. No.: 659,402

[22] Filed: Oct. 10, 1984

[51] Int. Cl.[4] .............................................. A61B 10/00
[52] U.S. Cl. .................................... 128/660; 358/249
[58] Field of Search ................................ 128/660–663; 73/618–626; 358/245, 249; 248/585, 580, 581, 639, 648, 653–654, 660–667, 669, 676–678

[56] References Cited

U.S. PATENT DOCUMENTS

| | | | |
|---|---|---|---|
| 3,044,346 | 7/1962 | Fieux | 248/662 X |
| 3,547,390 | 12/1970 | Mehr | 248/585 X |
| 3,699,250 | 10/1972 | Bunting | 358/249 X |
| 4,103,677 | 8/1978 | Lansiart et al. | 128/660 |
| 4,260,376 | 4/1981 | Litel et al. | 358/249 X |
| 4,543,739 | 10/1985 | Zerhoch et al. | 248/676 X |

OTHER PUBLICATIONS

Northeved, A. et al., "An Automatic Spherical Section Scanner", Ultrasound in Medicine & Biology, vol. 1, No. 2, (1974), pp. 183–186.

*Primary Examiner*—Kyle L. Howell
*Assistant Examiner*—Francis J. Jaworski
*Attorney, Agent, or Firm*—Watts, Hoffmann, Fisher & Heinke Co.

[57] ABSTRACT

An ultrasonic medical diagnostic imaging system is disclosed having an articulated mounting structure for supporting a television image display monitor component. The structure includes a first arm mounted for pivotal movement about a first substantially vertical axis. A second arm is pivotally connected to the first arm for movement about a second movable vertical axis displaced from the first axis. Journaling structure couples the second arm to one axis side of the television monitor for tilting rotation of the monitor about a substantially horizontal axis. Elevator structure defines a vertical travel path of monitor position. Rack apparatus associated with the elevator facilitates locking the monitor at intermediate points along its vertical travel path. Spring bias apparatus applies an upward biasing force to counterbalance the weight of the monitor and the other vertically movable portions of the structure. Damping apparatus frictionally inhibits unattended movement of the monitor. Stop means inhibits motion of the support structure to prevent overtravel.

35 Claims, 11 Drawing Figures

ULTRASONIC IMAGE DISPLAY MOUNTING

TECHNICAL FIELD

This invention relates generally to the field of ultrasonic medical diagnostic imaging, and more particularly to a mechanism for movably supporting a television image display monitor component of an ultrasonic imaging system.

BACKGROUND ART

It is well known to utilize ultrasound wave propagation for medical diagnostic imaging. Systems for ultrasonic diagnostic imaging include an ultrasonic transducer probe, which responds to electrical transmission signals to propagate ultrasonic energy into a subject such as a human patient. The transducer responds to incident energy resulting from ultrasonic echoes within the subject to produce echo signals representing the detected echoes. Imaging circuitry processes the echo signals to produce imaging signals representing an image corresponding to the received echoes. A monitor coupled to the imaging circuitry responds to the imaging signals to produce a visual display of the patient's internal body structure as indicated by the received ultrasonic echoes.

In the past, the monitor has been fixedly mounted as part of a main operator's console. The console also contained the system controls. The ultrasonic transducer probe was flexibly attached to the console, which additionally housed the operating circuitry for the system.

Ultrasonic imaging systems are described, for example, in U.S. Pat. No. 4,409,982, issued on Oct. 18, 1983 to Plesset, et al entitled "Ultrasonic Step Scanning Ultilizing Curvilinear Transducer Array", and U.S. Pat. No. 4,014,207, issued on Mar. 29, 1977, to Meyer et al and entitled "Sector Scanning Ultrasound Inspection Apparatus", both of which patents are expressly incorporated by reference.

In some types of ultrasonic systems, an operator manipulates the probe about the patient's body while gradually building up an image on the monitor screen, for example in a technique, described in the above incorporated Meyer et al patent. In other types of studies, the operator holds a probe against a portion of the patient's body, while watching an image developed in real time on the monitor screen. An example of this latter type of operation is set forth in the above incorporated Plesset et al patent.

The placement of the monitor in the main console forced the operator to divide his or her attention between the patient and the monitor. The operator was required to assure that the probe was properly manipulated or placed with respect to the patient's body, while at the same time observing the development or production of the image. In so widely dispersing the operator's attention, the system rendered the operator unable to devote his or her full attention to any of the patient, the monitor or the controls. This limitation sometimes reduced both operation efficiency and image quality, and caused operator inconvenience.

More recently, it has been proposed to movably mount a television monitor in an ultrasonic examination system. According to one proposal, the monitor was mounted near one end of a single straight arm which was pivotally attached to the console for rotation about a fixed vertical axis. The monitor was itself pivotally mounted near the free end of the single arm for rotation about another vertical axis. The arm and attached monitor were vertically adjustable to one of two positions about four inches apart.

While providing for some degree of flexibility of monitor positioning, this structure suffered from several disadvantages.

Its very limited vertical adjustability made it difficult for an operator to view the monitor in both a standing and sitting posture. The problem was exacerbated partly because there was no capability for tilting the monitor face.

The proposed structure, using only the single arm, maintained the monitor at a non-adjustable, fixed distance from the console.

It was also often inconvenient to position the monitor for the patient's viewing if desired.

Sometimes, the patient would have to be moved or shifted to accommodate the limited flexibility of monitor positioning.

Unusually tall and short operators would sometimes have difficulty in accommodating to the system.

In short, the mounting apparatus of this proposal failed to overcome many of the disadvantages of the older fixed monitor systems. The wide dispersal of operator attention was still required.

It is an object of this invention to provide a mounting apparatus for an ultrasonic display image monitor having sufficient flexibility and control for optimally positioning the monitor for all operators, patients and types of ultrasonic studies.

DISCLOSURE OF INVENTION

The foregoing disadvantages of the prior art are reduced or eliminated by an ultrasonic medical diagnostic examination system having an improved television display mounting arrangement.

The system includes an ultrasonic transducer probe being capable of propagating ultrasound into a subject in response to electrical stimuli, and for producing electrical signals in response to received ultrasonic echoes. Imaging circuitry processes the transducer-produced signals and generates imaging electrical signals describing an image of internal body structure as evidenced by the ultrasonic echoes. A television monitor is connected to the imaging circuitry to provide a visual display of the ultrasonically derived image.

In accordance with this invention, the monitor is supportively and flexibly mounted by way of an articulated supporting structure including a plurality of interconnected arms. The multiplicity of the arms provides for superior flexibility in positioning the monitor relative to the console, patient and operator, and for adjusting its distance from the console.

The articulated supporting structure also includes apparatus providing for tilting movement of the monitor about a horizontal axis. This feature assists an operator in conveniently viewing the monitor from both standing and seated positions, and accommodates operators of different heights. It also facilitates orienting the monitor for viewing by the patient where desired.

These advantages are further enhanced by an elevator structure coupled to the articulated support structure for enabling adjustment of monitor height over a substantial vertical range of travel. According to a more specific feature, a locking structure is provided in conjunction with the elevator mechanism to position the monitor at any of a set of intermediate locations over the vertical range of travel.

More specifically, an embodiment of the invention includes a first arm pivotally connected to a base structure for rotation about a first vertical axis. A second arm is pivotally attached to the first arm for rotation about a second movable vertical axis displaced from the first vertical axis. Journaling structure attached to the second arm is coupled to the monitor and supports the monitor for rotative tilting motion about a substantially horizontal axis.

In accordance with another specific feature, damping apparatus is interposed between interconnected portions of arms to frictionally inhibit unintended monitor movement between deliberate operator adjustments. Once the operator positions the monitor, the friction damping means causes it to remain stationary until moved again by operator intervention. No positive locks are needed. The damping torque is adjustable.

Another specific aspect of the invention comprises placement of all or a substantial portion of the ultrasonic system controls on or attached to the monitor, such that the controls ride with the monitor on the articulated supporting structure and are easily actuated by an operator simultaneously viewing the display on the monitor screen.

Another feature resides in the provision of the articulated supporting structure with stop means for inhibiting motion of the articulated support structure to avoid undesirable overtravel. According to a more specific aspect the stop means operates to limit movement to a degree which varies as a function of the elevation of the monitor.

The articulated support structure in accordance with this invention mounts the monitor in a way defining a substantially horizontal plane of permitted monitor motion. The elevator structure enables vertical adjustment of that defined horizontal plane through a substantial range of travel. Means is also provided for tilting the monitor about a horizontal axis, further increasing system flexibility.

The monitor can thus be raised up or down, and even rotated through nearly a full circle, in back, front or to the side of the console. The system enables placement of monitor, controls, and patient within a narrow geometrical region of operator concentration, and eliminates the wide dispersal of operator attention among console, monitor and patient. The system of this invention eliminates the need to shift the patient to accommodate fixed or limited positions of console and monitor. The monitor can be easily adjusted by the operator, and will stay in place between adjustments without any need for setting locks.

An operator can adjust the monitor and bring its image, along with system controls, in line with his or her view of the patient, wherever the operator needs to be for best eye and hand contact. An operator can sit or stand, operate the probe from either side or from above the patient's head, whatever is optimal for the study.

This invention will be understood in more detail by reference to the following specific description and to the drawings, in which:

BEST MODE FOR CARRYING OUT THE INVENTION

Figure 1:
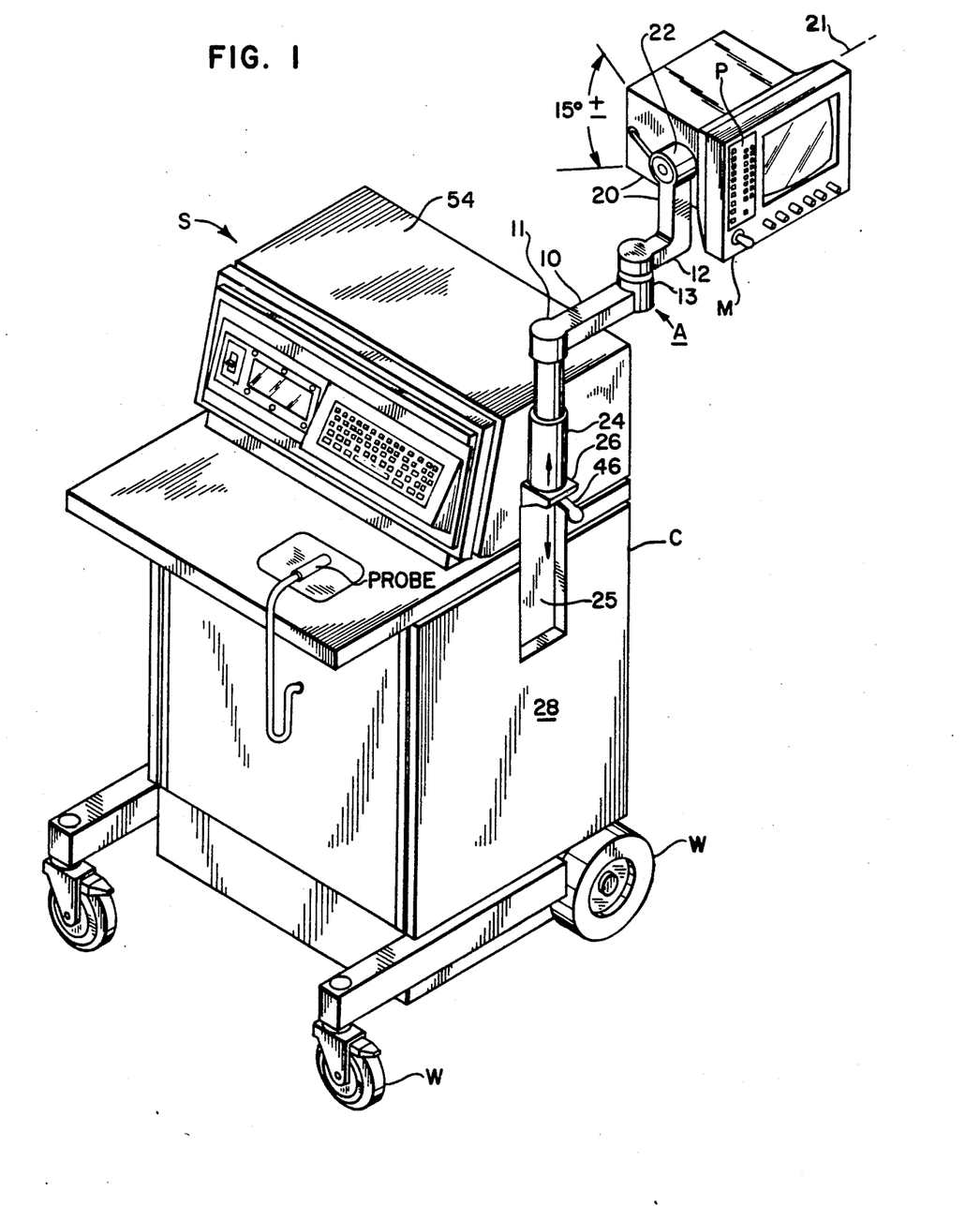
FIG. 1 is an isometric drawing of a system incorporating the present invention.
Figure 1A:
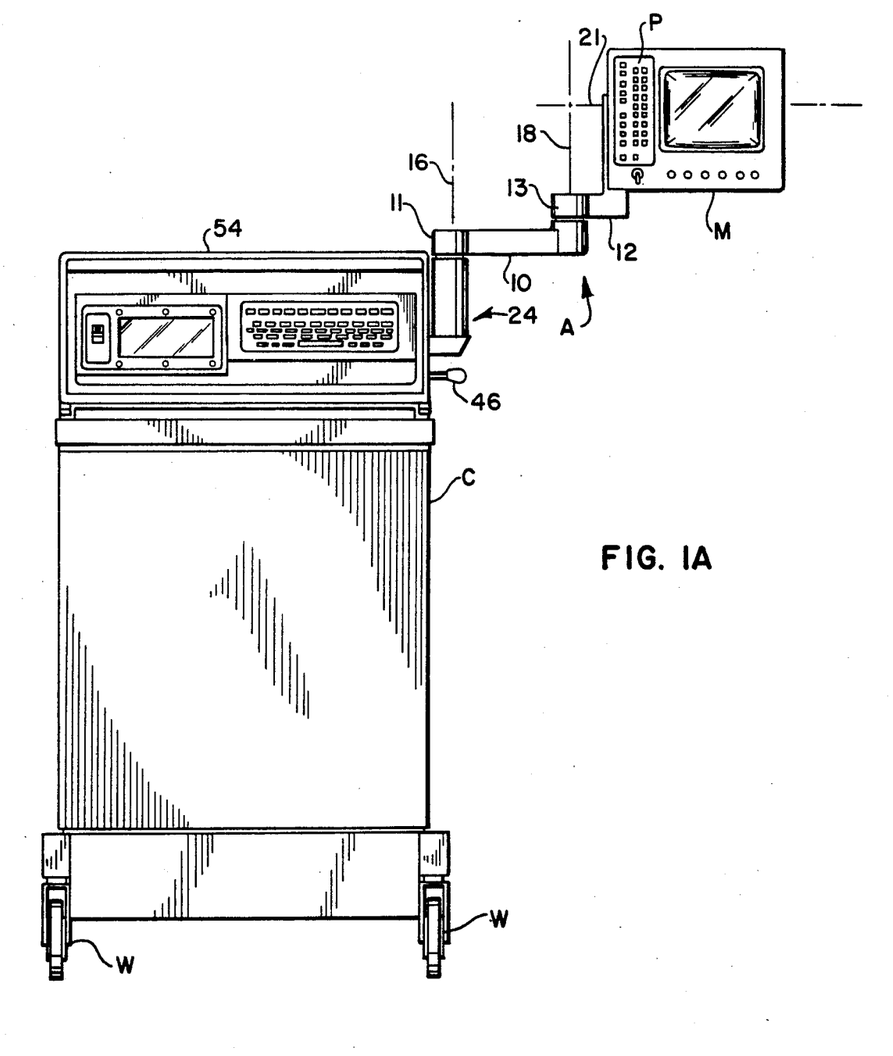
FIG. 1A is a front elevational view showing a system incorporating the present invention.

FIGS. 1 and 1A illustrates an ultrasonic system S for performing medical diagnostic ultrasonic imaging studies. The system S includes an ultrasonic transducer probe of known construction and responsive to electrical pulsing signals to propagate incident ultrasonic energy into a subject such as a human patient. The transducer responds to ultrasonic echoes from the incident energy to produce echo indicating signals.

The transducer probe is electrically coupled in known fashion to imaging circuitry of known type housed within a console C. Echo signals from the transducer are transmitted to the imaging circuitry, which processes them into imaging signals representing an image corresponding to the ultrasonic echoes. The imaging circuitry is electrically coupled to a monitor M, which produces a visible image on its screen corresponding to the received echoes.

The monitor M includes a control panel P electrically coupled for controlling the imaging and other circuitry of the ultrasonic system located within the console C.

The monitor M is movably and supportively coupled to a base or frame portion of the sole C by means of an articulated support structure A. See FIGS. 1, 1A, 2, 2A and 3.

The system S is rendered mobile by its provision with a set of wheels W.

Details of examples of ultrasonic imaging systems into which the present invention may suitably be incorporated are set forth for example in the above incorporated Plesset et al and Meyer et al patents. Accordingly, discussion of such details here is not warranted.

Figure 2:
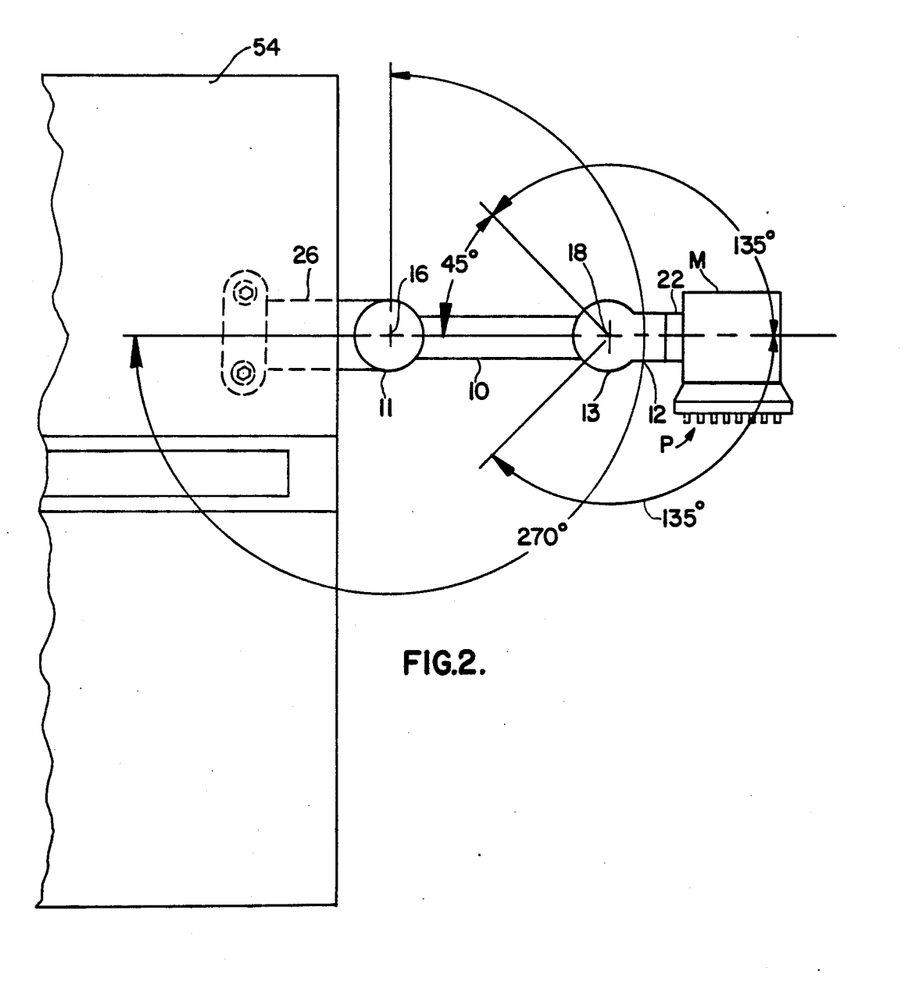
FIG. 2 is a plan view of a portion of the system of FIG. 1.
Figure 2A:
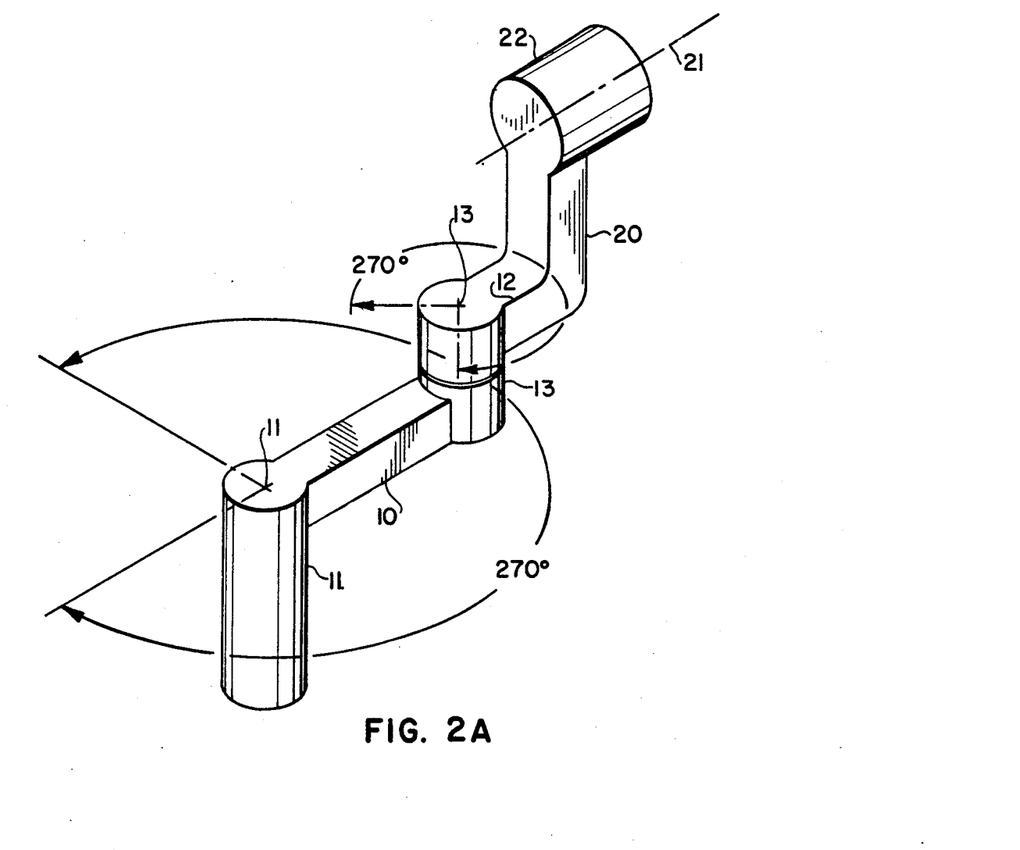
FIG. 2A is an isometric drawing of a portion of the system shown in FIG. 2.
Figure 3:
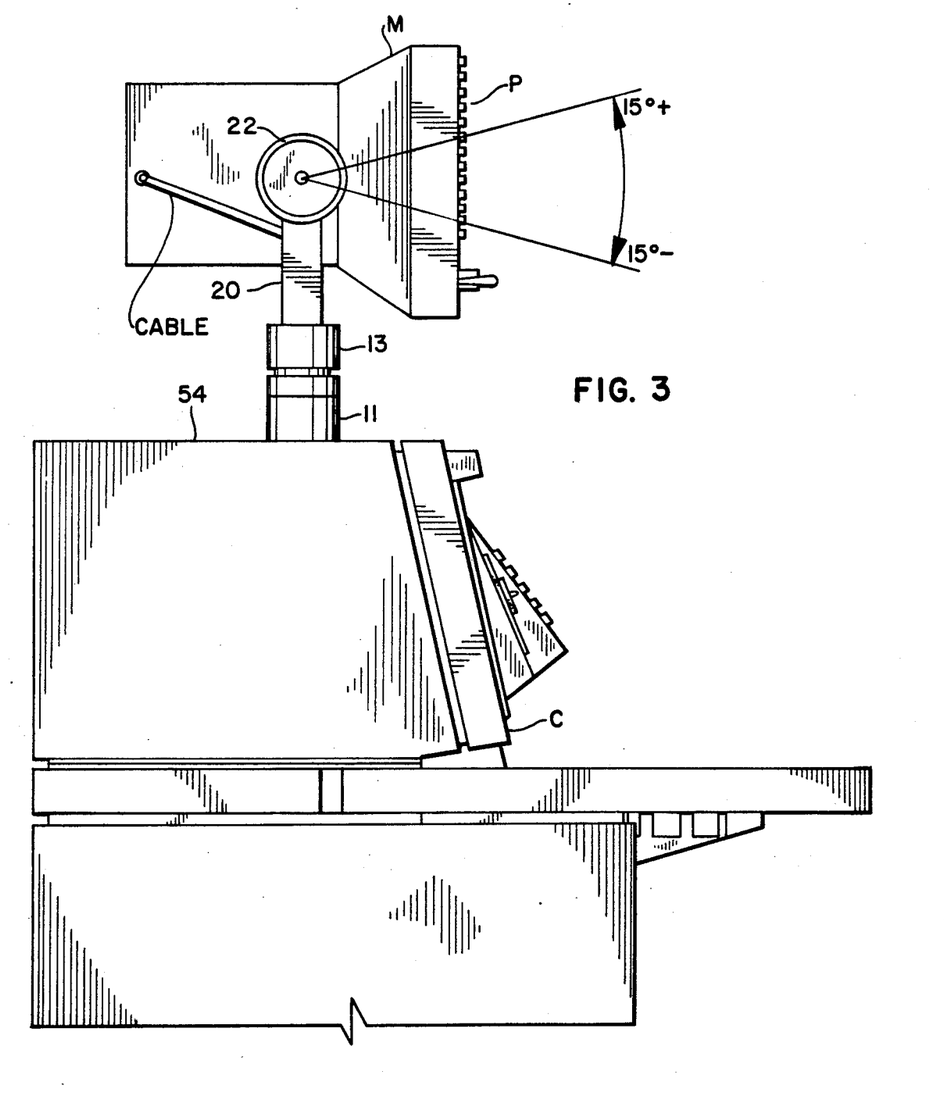
FIG. 3 is a left side elevational view of a portion of the system of FIG. 1.
Figure 4:
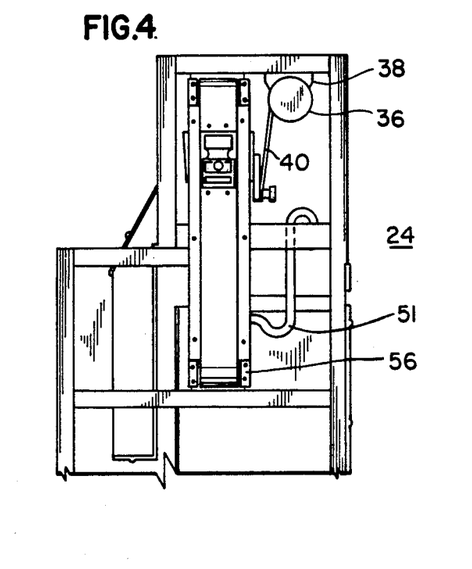
FIG. 4 is a right side elevational view of a portion of the system of FIG. 1.
Figure 5:
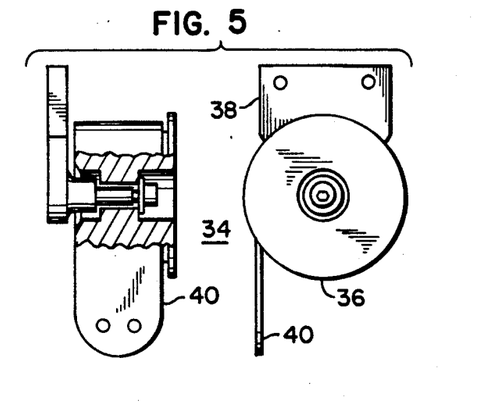
FIGS. 5-9 are detailed drawings, partly in cross-section, of portions of the system of FIG. 1.

The articulated arm structure A includes a first arm 10, and a second arm 12. The first arm 10 is pivotally coupled to a base or frame portion of the console C by a pivot assembly 11 for rotation about a first vertical axis 16. The second arm 12 is pivotally coupled to the outer end of the first arm 10 by a pivot assembly 13 for rotation about a second vertical axis 18, which is movable and displaced from the first axis 16. The second arm 12 is generally L-shaped in configuration. Its upstanding leg portion 20 is coupled by means of journaling structure 22 to one side of the television monitor M. The second arm 12 and journaling structure 22 support the monitor M for tilting motion about a substantially horizontal axis of rotation 21.

The pivotal motion of the first and second arms 10, 12 about vertical axes 16, 18 defines a horizontal plane in which the monitor M can be moved. The journaling structure 22 adds a degree of rotative freedom of the monitor about a horizontal axis such that the monitor screen may be tilted upwardly or downwardly as desired. An operator can effect the described monitor motion by simply positioning the monitor M manually.

Each of the first and second arms 10, 12 is approximately eight inches in length and is made of aluminum.

Means is provided for vertically adjusting the position of the articulated support structure A and of the monitor M. Elevator structure 24 is coupled between (1) the inner end of the first arm 10 and pivot assembly 11 and (2) base or frame portion of the console C, and defines a vertical path of movement for the first arm 10, and the remainder of the articulated structure and attached monitor, of slightly more than eleven inches. See FIGS. 4-6 and 8.

The elevator assembly 24 comprises a support member 26 extending through an opening 25 in a side panel 28 of the console C and connected to the pivot assembly 11.

Figure 6:
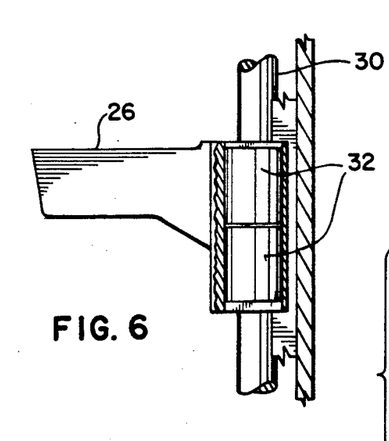

The elevator assembly 24 (see FIGS. 4-6) include linear ball bearing guides 30 which allow the support member 26 to slide up and down on a set of linear bearings 32 (FIG. 6). Four linear bearings 32 are used to minimize wear and reduce friction due to the overhanging load of the articulated support structure A and of the monitor M.

Structure is provided for counterbalancing the weight of the articulated structure A and of the monitor M to reduce the manual effort necessary to effect desired vertical motion of the monitor M. A spring roller assembly 34, (FIGS. 4 and 5) including a roller 36, a bracket 38 and a negator spring 40 is provided for this purpose and is attached to the console frame or base. The negator spring is coupled between the roller 36 and the support member 26, and provides a substantially constant upward force on the support member 26, tending to neutralize the downward force of the weight of the articulated arm structure A and the monitor M. In practice, it has been found that a negator spring 40 suitably exerts a substantially constant upward force of approximately 33 pounds. This value is choosen to be about 2 pounds greater than the combined weight of the articulated structure A and monitor M. The force of the spring 40 thus tends to impart a gentle upward net vertical bias to the vertically movable components when the elevator assembly 24 is released such that the articulated structure and monitor are permitted to rise or fall by action of the elevator assembly 24. Up and down motion of the monitor and articulated structure is effected manually.

Electrical cabling coupling the monitor M and control panel P with the console C is carried in appropriate recesses (not shown) in the arms 10, 12, and extends through the elevator structure into the console. A service loop 51 of cable is provided to accommodate elevator motion up and down.

Figure 7:
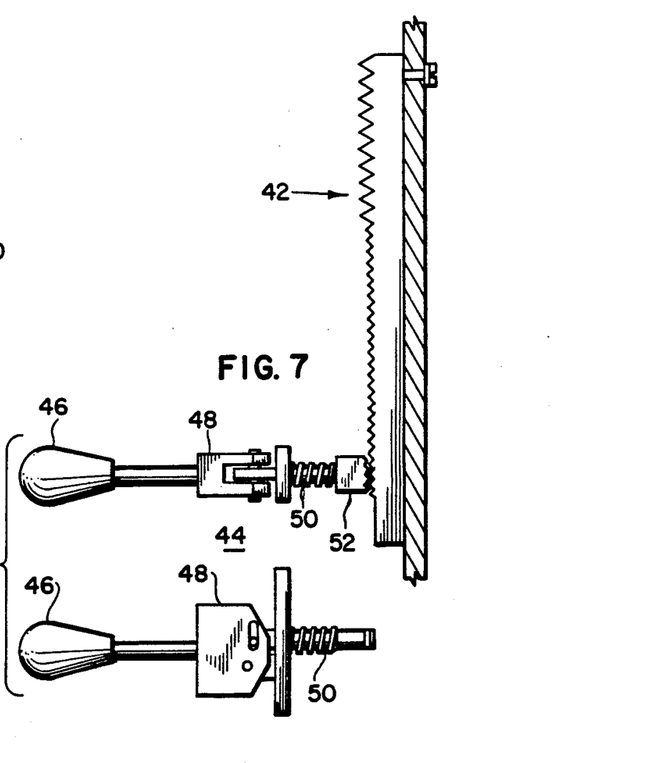
Figure 8:
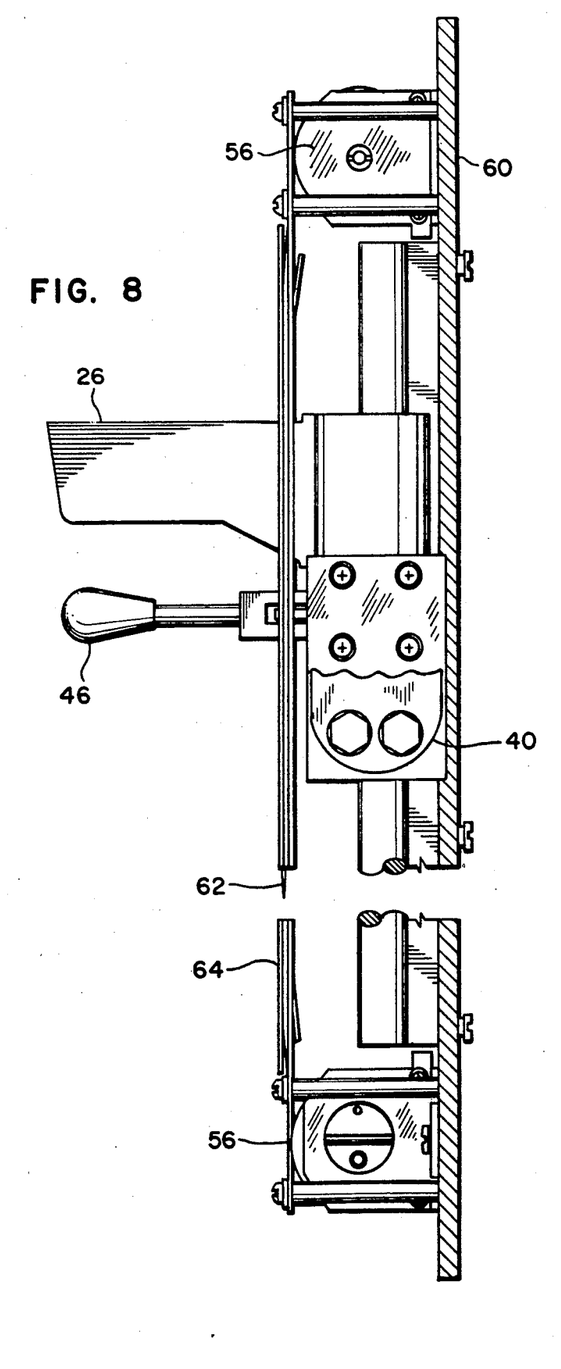

Structure associated with the elevator assembly is provided to facilitate locking of the vertical elevation of the monitor at any of a set of points along its vertical path of travel as defined by the elevator assembly. As shown in FIGS. 7 and 8, a rack 42 is mounted between the linear ball guides which allow the unit to slide up and down on the linear bearings. Opposite the rack 42 is a locking device 44 including a lever 46, a cam lock plate 48, a spring 50 and a locking member 52.

By action of the lever 46 and the cam lock plate 48, the locking member 52 selectively engages the rack 42 to lock the elevator assembly at any of a predetermined set of points along its vertical travel path, as determined by the tooth and groove configuration of the rack 42. The locking device 44 is constructed to facilitate locking the mechanism against vertical motion at at least two positions along its travel path. A first position is located such that the second arm 12 can clear a top surface 54 of the console by approximately ¾ inch.

A second desirable predetermined locking point is chosen at a location such that the first arm 10 will clear the top surface 54 by approximately ¾ inch, both arms 10, 12 thus clearing the surface 54. This arrangement facilitates obtaining maximum rotative movement of the first and second arms by positioning them to respectively clear the upper surface of the console. This feature also permits the monitor to be advanced a total of about 16 inches across the top of the console when desired.

A spring roller slot cover assembly 56 is provided to cover the opening 25 in the side panel of the console C as the support member 26 moves up and down by the action of the elevator assembly. More specifically, (see FIG. 8) two assemblies 56 are attached to each end of a mounting plate 60. As the support member 26 is moved, a portion 62 of cover material slides in tracks 64 to maintain a covering over the opening, to inhibit dust and other contamination of the equipment within the console.

Figure 9:
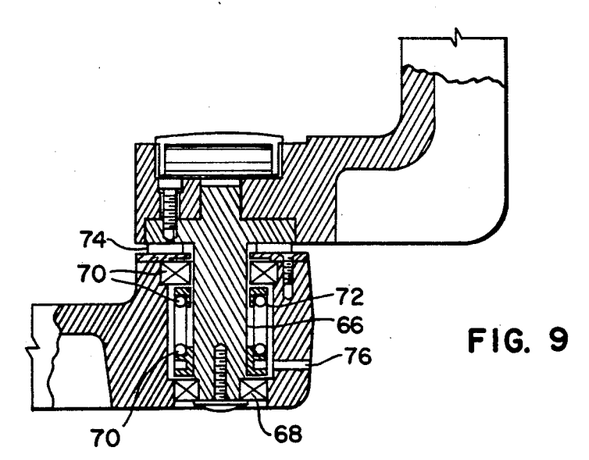

The detailed structure of the pivot assemblies 11, 13 at the axes 16, 18 is illustrated in FIG. 9. A pivot shaft 66 extends through the center of the pivot assembly. The pivot shaft 66 is fixed to one of the arms which are interconnected at the pivot and rotates with that arm. A duplex ball bearing assembly 68, 70 facilitates rotation of the pivot shaft 66 relative to the arm to which it is not positively connected. An adjustable spring 72 is situated between the ball bearings and loads the pivot shaft against a friction surface 74 between the two arms which are interconnected at the pivot.

As the arm fixed to the pivot shaft turns, the lower portion of that arm presses against the friction material which is trapped on the pivot shaft between the arms.

The loading provided by the adjustable spring inside the lower pivot section can be increased or decreased in known fashion by insertion of a tool through the slots provided and indicated at 76. The spring load directly affects the loading on the friction material. This in turn determines the friction damping torque load thus provided, for damping relative motion between the arms interconnected by the pivot assembly.

Preferably, the friction damping torque about the first vertical axis 16 is preset to have a value approximately twice the corresponding torque provided with respect to rotation about the second vertical axis 18. This feature inhibits buckling of the arm assembly, by compensating for the fact that, during monitor manual motion, there is about twice as much leverage applied about the first vertical axis 16 as about the second vertical axis 18, due to the two arms 10, 12 being approximately equal in length. If this torque is set properly for these pivot axes, both pivots will share equal motion when the monitor is moved.

Each pivot assembly 11, 13 is provided with a specific stop for limiting relative rotation of the associated arms. These stops each comprise precision dowel pins made of stainless steel which keep the associated components confined to a limited relative rotational range.

The first arm 10 is thereby limited at its inner end to rotational movement of approximately 270° with respect to the console C and about the axis 16. More specifically, as viewed in FIG. 2, the first arm 10 is movable clockwise between the twelve o'clock and nine o'clock positions, with the clockwise 90° between nine o'clock and twelve o'clock being forbidden.

The pivot assembly 13 coupling the first and second arms 10, 12 is also provided with stop means of known type. More specifically, the second arm 12 is rotatable with respect to the first arm 10 by ±135°, either way from the fully extended position indicated in FIG. 2. The 90° stopped or forbidden region is arranged so that the second arm 12 can approach the lower inner arm 10 no closer than 45° from either side.

The journaling structure 22 also contains stops for limiting monitor tilting motion. The monitor is permitted to tilt upwardly or downwardly by 15° from a position in which its screen is substantially vertical.

As mentioned above, the elevator structure and its associated rack locking device are designed to establish at least three elevations for the monitor M. The uppermost position is chosen such that both the first and second arms 10, 12 are above the upper surface of the console C. At this position, both arms are free to rotate relatively over their full unstopped range as described above.

In a second vertical position, the second arm 12 is positioned to clear the top of the console C, but the first arm 10 is below the top surface, such that it can move only 180°, i.e., clockwise from twelve to six o'clock as shown in FIG. 2.

In this second example, it will be seen that, when the first arm 10 is at the twelve o'clock position, the second arm 12 can rotate clockwise between approximately the 7:30 and 4:30 positions. When the first arm 10 is at the six o'clock position, the second arm is free to rotate clockwise ±135° between approximately the 1:30 and 10:30 positions.

In a lower position, neither the first or second arm 10, 12 can clear the top of the console. Accordingly, the motion of the first arm 10 is limited as described in connection with the previous example, i.e., to 180°.

The permitted motion in this third example can be readily deduced in a manner analogous to that explained in connection with the second, keeping in mind the limits of relative rotation between the first and second arms about the pivot assembly 13.

Preferably, the system is provided with appropriate bumpers of known type (not shown) for cushioning any impingement of the arms or monitor with portions of the console.

It will be seen that, by virtue of the articulated arm structure, the monitor can be located behind, in front of, to the side, or directly over, the console C. This system enables placement of the monitor, control panel and patient within a narrow geometrical region of operator concentration, and eliminates the wide dispersal of operator attention among console, monitor and patient that obtained in the practice of the prior art. The patient need not be shifted to accommodate limited flexibility of the monitor. Rather, the monitor can assume virtually any desirable position with respect to a patient. The monitor can easily be manually adjusted by the operator, and, once the operator has desirably positioned the monitor, the friction damping structure will maintain it in that position until the operator chooses to intervene and readjust the monitor position. There is no need for the operator to adjust or set any locks to secure the monitor in position. The operator can perform studies in either a sitting or standing position, without sacrificing visibility of the monitor. This system accommodates both unusually tall and short operators, and can position the monitor generally whereever it is required for any type of study.

The foregoing specific description of the best mode for carrying out this invention is intended as illustrative, rather than exhaustive, of the invention. It is to be recognized that those of ordinary skill in the relevant art will be able to make certain additions, deletions or modifications to the embodiment disclosed here without departing from the spirit or the scope of the invention, as set forth in the appended claims.

What is claimed is:

1. An ultrasonic examination system comprising:
    (a) an ultrasonic transducer means responsive to electrical signals to propagate ultrasonic energy, and responsive to the receipt of ultrasonic echoes to generate electrical signals indicative of such echoes;
    (b) imaging circuitry including transmission circuitry coupled to said transducer means for generating electrical signals to actuate the transducer to propagate ultrasonic energy, and receiving circuitry responsive to echo indicating signals generated by said transducer means in response to ultrasonic echoes to produce imaging electrical signals representing an image corresponding to said echoes;
    (c) a monitor electrically coupled to said receiving circuitry for producing a visual image corresponding to said received echoes in response to said imaging signals;
    (d) base means;
    (e) articulated support means comprising a plurality of pivotally serially interconnected arms for supportively coupling said monitor for movement with respect to said base means, and
    (f) an array of controls electrically coupled to control at least part of the operation of said imaging circuitry, in addition to control of said monitor, said array being mechanically coupled to move with said monitor.

2. The system of claim 1, wherein said articulated support means further comprises:
    means for friction damping of movement of said articulated support means.

3. The system of claim 1, wherein said articulated support means comprises:
    structure for mounting said monitor for movement in a defined substantially horizontal plane.

4. The system of claim 3, further comprising:
    elevator means defining a vertical travel path and being coupled between said articulated support means and said base structure for effecting vertical adjustment of said substantially horizontal defined plane of monitor movement.

5. The system of claim 4, wherein said articulated support means further comprises:
    means for mounting said monitor for rotational movement about a substantially vertical axis.

6. The system of claim 5, wherein said articulated support means further comprises:
    means for mounting said monitor for rotational movement with respect to said articulated support means and about a substantially horizontal axis.

7. The system of claim 4, wherein said elevator means further comprises:
    means for locking the location of said defined horizontal plane of monitor movement at one of a predetermined set of elevations.

8. The system of claim 7, wherein said articulated support means further comprises:

stop means for inhibiting motion of said monitor to a degree which is a function of said elevation.

9. The system of claim 4, further comprising:
means for applying an upward biasing force on said monitor.

10. The system of claim 9, wherein:
said biasing force applying means applies an upward biasing force on said monitor in excess of the weight of said monitor.

11. The system of claim 4, further comprising:
means associated with said elevator means for locking said articulated arm means at a predetermined intermediate point along said vertical travel path defined by said elevator means.

12. The system of claim 1, wherein said articulated support means further comprises:
stop means for inhibiting motion of said monitor to prevent overtravel by said monitor.

13. The system of claim 1, wherein said articulated support means comprises:
(a) a first arm coupled to said base structure for pivotal motion about a first substantially vertical axis, and
(b) a second arm pivotally coupled to said first arm for rotation about a second vertical axis displaced from said first vertical axis.

14. The system of claim 13, wherein said articulated support means further comprises:
journaling means coupled between said second arm and said monitor for mounting said monitor for pivotal tilting movement about a substantially horizontal axis.

15. The system of claim 14, wherein:
said journaling means is coupled to and supports the monitor on only one side of said monitor.

16. The system of claim 13, further comprising:
(a) friction damping means for damping said rotation about said first and second vertical axes, and
(b) the degree of friction damping being different for rotation about said first axis than about said second axis.

17. The system of claim 16, wherein:
the torque of friction damping about said first vertical axis is about twice the damping torque about said second axis.

18. The system of claim 16, further comprising:
means for adjusting the torque of said friction damping apparatus.

19. The system of claim 1, further comprising:
elevator means coupled to said articulated support means for facilitating vertical adjustment of said articulated support means and said monitor with respect to said base means.

20. The system of claim 1, further comprising:
said imaging circuitry control panel being positioned to ride with said monitor on said articulated support means.

21. The system of claim 1, wherein:
(a) said system further comprises an operating console, and
(b) said base means comprises a portion of said console.

22. An ultrasonic examination system comprising:
(a) an ultrasonic transducer means responsive to electrical signals to propagate ultrasonic energy, and responsive to the receipt of ultrasonic echoes to generate electrical signals indicative of such echoes;
(b) transmission circuitry coupled to said transducer means for generating electrical signals to actuate the transducer to propagate ultrasonic energy, and receiving circuitry responsive to echo indicating signals generated by said transducer means in response to ultrasonic echoes to produce imaging electrical signals representing an image corresponding to said echoes;
(c) a monitor coupled to said receiving circuitry for producing a visual image corresponding to said received echoes in response to said imaging signals;
(d) base means;
(e) articulated support means for supportively coupling said monitor movably with respect to said base for a combination of movement in a substantially horizontal plane and rotationally with respect to said base and about a substantially horizontal axis.

23. An ultrasonic examination system comprising:
(a) an ultrasonic transducer means responsive to electrical signals to propagate ultrasonic energy, and responsive to the receipt of ultrasonic echoes to generate electrical signals indicative of such echoes;
(b) transmission circuitry coupled to said transducer means for generating electrical signals to actuate the transducer means to propagate ultrasonic energy, and receiving circuitry responsive to signals generated by said transducer in response to ultrasonic echoes to produce imaging electrical signals representing an image corresponding to said echoes;
(c) a monitor coupled to said receiving circuitry for producing a visual image corresponding to said received echoes in response to said imaging signals;
(d) base means;
(e) movable supporting means coupled between said monitor and said base means for defining a substantially horizontal plane of monitor movement, elevator means for effecting vertical adjustment of said horizontal plane so defined over a vertical travel path, and means for locking said elevator means to define said substantially horizontal plane located at an intermediate point along said vertical travel path.

24. An ultrasonic examination system comprising:
(a) an ultrasonic transducer means responsive to electrical signals to propagate ultrasonic energy, and responsive to receipt of ultrasonic echoes to generate electrical signals indicative of such echoes;
(b) transmission circuitry coupled to said transducer means for generating electrical signals to actuate the transducer means to propagate ultrasonic energy, and receiving circuitry responsive to signals generated by said transducer in response to ultrasonic echoes to produce imaging electrical signals representing an image corresponding to said echoes;
(c) a monitor coupled to said receiving circuitry for producing a visual image corresponding to said received echoes in response to said imaging signals;
(d) a base means;
(e) articulated support means comprising a plurality of pivotally interconnected arms for movably coupling said monitor to said base, said articulated support means comprising:
(i) a first arm coupled to said base for pivotal motion about a first substantially vertical axis;

(ii) a second arm pivotally coupled to said first arm for rotation about a second movable vertical axis displaced from said first vertical axis;

(iii) journaling means coupled between said second arm and said monitor for mounting said monitor for pivotal tilting movement about a movable substantially horizontal axis;

(f) means for friction damping of movement of said articulated support structure;

(g) elevator means defining a vertical travel path and being coupled between said first arm and said base for effecting vertical adjustment of said articulated support means and said monitor;

(h) means for locking the vertical location of said articulated support means and said monitor;

(i) means for applying an upward biasing force on said articulated support means;

(j) a control panel electrically coupled to said imaging circuitry and positioned to ride with said monitor on a portion of said articulated support means.

25. An ultrasonic examination system comprising:

(a) an ultrasonic transducer means responsive to electrical signals to propagate ultrasonic energy, and responsive to the receipt of ultrasonic echoes to generate electrical signals indicative of such echoes;

(b) transmission circuitry coupled to said transducer means for generating electrical signals to actuate the transducer to propagate ultrasonic energy, and receiving circuitry responsive to signals generated by said transducer means in response to ultrasonic echoes to produce imaging electrical signals representing an image corresponding to said echoes;

(c) a monitor electrically coupled to said receiving circuitry for producing a visual image corresponding to said imaging signals;

(d) a base means;

(e) an articulated support means for supportively coupling said monitor for movement with respect to said base means;

(f) elevator means defining a travel path having a vertical component for raising and lowering said monitor, and (g) stop means for inhibiting motion of said monitor to a degree which is a function of the elevation of said monitor.

26. An ultrasonic examination system comprising:

(a) an ultrasonic transducer means responsive to electrical signals to propagate ultrasonic energy, and responsive to the receipt of ultrasonic echoes to generate electrical signals indicative of such echoes;

(b) transmission circuitry coupled to said transducer means generating electrical signals to actuate the transducer to propagate ultrasonic energy, and receiving circuitry responsive to signals generated by said transducer means in response to ultrasonic echoes to produce imaging electrical signals representing an image corresponding to said echoes;

(c) a monitor electrically coupled to said receiving circuitry for producing a visual image corresponding to said received echoes in response to said imaging signals;

(d) a base means;

(e) articulated support means comprising a plurality of pivotally interconnected arms for supportively coupling said monitor for movement with respect to said base, said articulated support means including a first arm coupled to said base means for pivotal motion about a first substantially vertical axis, a second arm pivotally coupled to said first arm for rotation about a second vertical axis displaced from said first vertical axis and friction damping means for damping said rotation about said first and second vertical axes wherein the degree of friction damping is different for rotation about said first axis than about said second axis.

27. The system of claim 26, wherein:
the torque of friction damping about said first axis is about twice the damping torque about said second axis.

28. The system of claim 26, further comprising:
means for adjusting the torque of said friction damping.

29. An ultrasonic examination system comprising:

(a) an ultrasonic transducer means responsive to electrical signals to propagate ultrasonic energy, and responsive to receipt of ultrasonic echoes to generate electrical signals indicative of such echoes;

(b) transmission circuitry coupled to said transducer means for generating electrical signals to actuate the transducer means to propagate ultrasonic energy, and receiving circuitry reponsive to signals generated by said transducer in response to ultrasonic echoes to produce imaging electrical signals representing an image corresponding to said echoes;

(c) a monitor coupled to said receiving circuitry for producing a visual image corresponding to said received echoes in response to said imaging signals;

(d) a base;

(e) articulated support means comprising a plurality of pivotally interconnected arms for supportively coupling said monitor to said base, said articulated support means comprising:

(i) a first arm coupled to said base for pivotal motion about a first substantially vertical axis;

(ii) a second arm pivotally coupled to said first arm for rotation about a second movable substantially vertical axis displaced from said first vertical axis;

(iii) means for mounting said monitor for pivotal tilting movement about a movable substantially horizontal axis;

(f) means for controllably preventing relative movement of at least part of said articulated support structure;

(g) elevator means defining a travel path having a vertical component for facilitating vertical adjustment of said monitor;

(h) a control array electrically coupled to control at least part of operation of said transmission and receiving circuitry in addition to said monitor and mechanically coupled to move with said monitor.

30. An ultrasonic examination system comprising:

(a) an ultrasonic transducer means responsive to electrical signals to propagate ultrasonic energy and responsive to receipt of ultrasonic echoes to generate electrical signals indicative of such echoes;

(b) imaging circuitry including transmission circuitry coupled to said transducer means for generating electrical signals to actuate the transducer means to propagate ultrasonic energy, and receiving circuitry responsive to signals generated by said transducer in response to ultrasonic echoes to produce imaging electrical signals representing an image corresponding to said echoes;

(c) a monitor coupled to said receiving circuitry for producing a visual image corresponding to said received echoes in response to said imaging signals;

(d) a base means;

(e) articulated support means comprising a plurality of pivotally interconnected arms for supportively coupling said monitor to said base, and (f) a control array electrically coupled to control both operation of said imaging circuitry and said monitor and mechanically coupled to move with said monitor.

31. An ultrasonic examination system comprising:

(a) an ultrasonic transducer means responsive to electrical signals to propagate ultrasonic energy, and responsive to receipt of ultrasonic echoes to generate electrical signals indicative of such echoes;

(b) imaging circuitry including transmission circuitry coupled to said transducer means for generating electrical signals to actuate the transducer means to propagate ultrasonic energy, and receiving circuitry responsive to signals generated by said transducer in response to ultrasonic echoes to produce imaging electrical signals representing an image corresponding to said echoes;

(c) a monitor coupled to said receiving circuitry for producing a visual image corresponding to said received echoes in response to said imaging signals;

(d) a base means;

(e) articulated support means comprising a plurality of pivotally interconnected arms for supportively coupling said monitor to said base, said articulated support means comprising:

(i) a first arm coupled to said base for pivotal motion about a first substantially vertical axis;

(ii) a second arm pivotally coupled to said first arm for rotation about a second movable substantially vertical axis displaced from said first vertical axis;

(iii) means for mounting said monitor for pivotal tilting movement about a substantially horizontal axis;

(f) elevator means defining a vertical travel path for facilitating vertical adjustment of said monitor;

(g) a control array electrically coupled to control said imaging circuitry and said monitor and positioned to move with said monitor on said articulated support means.

32. An ultrasonic examination system comprising:

(a) an ultrasonic transducer means responsive to electrical signals to propagate ultrasonic energy, and responsive to receipt of ultrasonic echoes to generate electrical signals indicative of such echoes;

(b) transmission circuitry coupled to said transducer means for generating electrical signals to actuate the transducer means to propagate ultrasonic energy, and receiving circuitry reponsive to signals generated by said transducer in response to ultrasonic echoes to produce imaging electrical signals representing an image corresponding to said echoes;

(c) a monitor coupled to said receiving circuitry for producing a visual image corresponding to said received echoes in response to said imaging signals;

(d) a base means;

(e) articulated support means comprising a plurality of pivotally interconnected arms for supportively coupling said monitor to said base, said articulated support means comprising:

(i) a first arm coupled to said base for pivotal motion about a first axis;

(ii) a second arm pivotally coupled to said first arm for rotation about a second movable axis displaced from said first vertical axis;

(iii) means coupled between said second arm and said monitor for mounting said monitor for tilting movement about a movable substantially horizontal axis;

(f) means for friction damping of movement of said articulated support structure;

(g) elevator means defining a vertical travel path for facilitating vertical adjustment of said monitor;

(h) means for locking the vertical location of said articulated support means and said monitor.

33. In an ultrasonic examination system including an ultrasonic transducer means responsive to electrical signals to propagate ultrasonic energy, and responsive to the receipt of ultrasonic echoes to generate electrical signals indicative of such echoes, transmission circuitry coupled to said transducer means for generating electric signals to actuate the transducer to propagate ultrasonic energy, and receiving circuitry responsive to signals generated by said transducer means in response to ultrasonic echoes to produce imaging electrical signals representing an image corresponding to said echoes, a monitor coupled to said receiving circuitry for producing a visual image corresponding to said received echoes in response to said imaging signals and a base means, the improvement comprising:

articulated support means comprising a plurality of pivotally and serially interconnected arms for supportively and movably coupling said monitor to said base and means for damping relative movement of said arms, said articulated support structure comprising a first arm coupled to said base for pivotal motion about a first substantially vertical axis, and a second arm pivotally coupled to said first arm for rotation about a second vertical axis displaced from said first vertical axis.

34. The improvement of claim 33, wherein said articulated support means further comprises:

journalling means coupled between said second arm and said monitor for mounting said monitor for pivotal tilting movement about a substantially horizontal axis.

35. The improvement of claim 33, further comprising:

elevator means coupled to said articulated support structure for effecting vertical adjustment of said articulated support structure and said monitor with respect to said base structure.

* * * * *